(12) United States Patent
Haight

(10) Patent No.: US 6,758,971 B1
(45) Date of Patent: Jul. 6, 2004

(54) SELF-PRIMING DIALYSIS FILTER

(75) Inventor: LeVoy G. Haight, West Jordan, UT (US)

(73) Assignee: Sorenson Development, Inc., Salt Lake City, UT (US)

(*) Notice: Subject to any disclaimer, the term of this patent is extended or adjusted under 35 U.S.C. 154(b) by 0 days.

(21) Appl. No.: 09/763,903

(22) PCT Filed: Aug. 26, 1999

(86) PCT No.: PCT/US99/19579

§ 371 (c)(1),
(2), (4) Date: Feb. 26, 2001

(87) PCT Pub. No.: WO00/12193

PCT Pub. Date: Mar. 9, 2000

Related U.S. Application Data

(60) Provisional application No. 60/098,318, filed on Aug. 28, 1998.

(51) Int. Cl.$^7$ .......................... B01D 29/00; B01D 29/11; B01D 63/06; B01D 63/08
(52) U.S. Cl. ............. 210/321.72; 210/136; 210/321.75; 210/321.78; 210/321.84; 210/321.87; 210/433.1; 210/435; 210/436; 210/446; 210/456; 210/472; 210/483; 210/484; 210/498
(58) Field of Search ........................... 210/136, 321.72, 210/321.75, 321.78, 321.84, 321.87, 433.1, 435, 436, 446, 456, 472, 483, 484, 498; 604/29

(56) References Cited

U.S. PATENT DOCUMENTS

| | | | |
|---|---|---|---|
| 4,311,587 A | 1/1982 | Nose et al. | 210/136 |
| 4,488,961 A | 12/1984 | Spencer | 210/136 |
| 4,738,668 A | 4/1988 | Bellotti et al. | 604/29 |
| 5,252,222 A | 10/1993 | Matkovich et al. | 210/650 |
| 5,258,127 A | 11/1993 | Gsell et al. | 210/767 |
| 5,439,587 A | 8/1995 | Stankowski et al. | |
| 5,622,626 A | 4/1997 | Matkovich et al. | 210/649 |

FOREIGN PATENT DOCUMENTS

GB  1 601 223  10/1981

*Primary Examiner*—John Kim
(74) *Attorney, Agent, or Firm*—TraskBritt

(57) ABSTRACT

A medical filter (11) is constructed as a container with an interior volume in open fluid communication with a patient connection element (31) and a transport connection element (39). Filter support structure (13) mounted within the interior is structured as a thin, perforated member (14) carrying hydrophilic filter medium (17). A first flow path directs spent dialysate from the patient across the surface of the filter medium (17) to the transport connection (39). A second flow path directs fresh dialyalysate from the transport connection (39) through the filter medium (17) and the perforated support structure (13) to the patient connection (31).

27 Claims, 4 Drawing Sheets

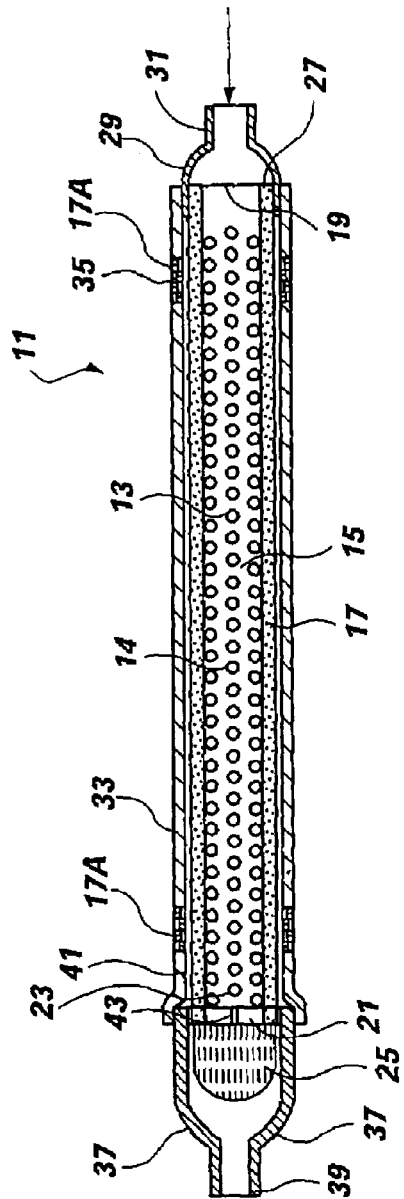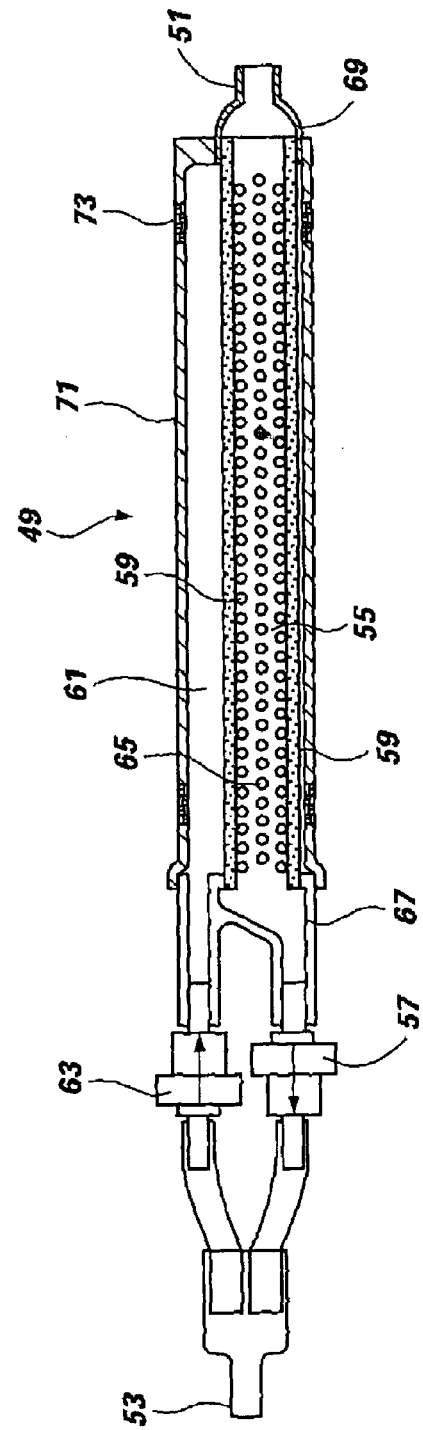

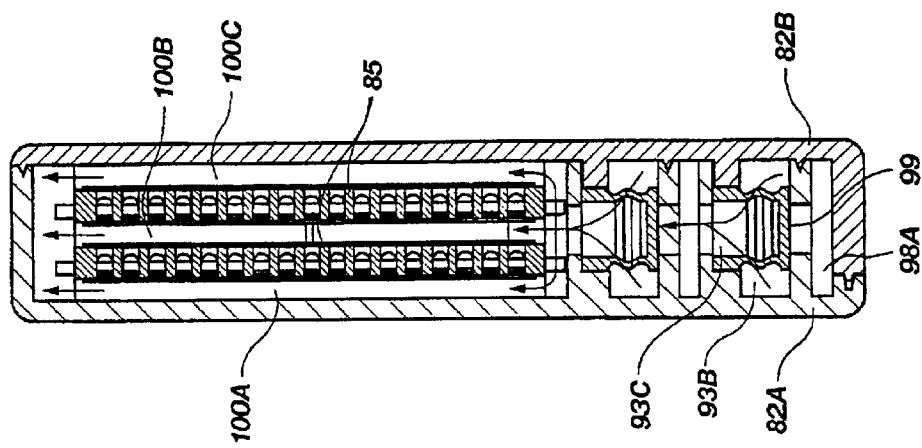
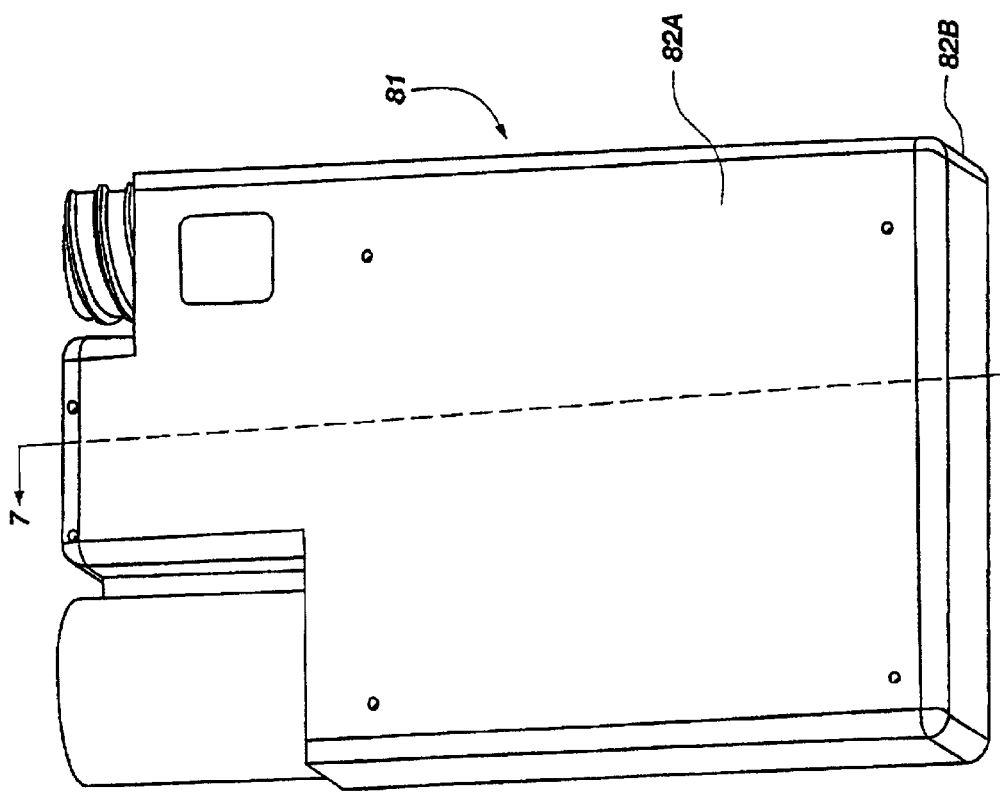

ns,971 B1

SELF-PRIMING DIALYSIS FILTER

PRIORITY CLAIM

This application claims the benefit of the filing date of U.S. Provisional Patent Application Serial No. 60/098,318, filed Aug. 28, 1998 for "SELF-PRIMING DIALYSIS FILTER."

TECHNICAL FIELD

This invention relates to kidney dialysis, and provides an improved filter system for home use dialysis procedures.

BACKGROUND ART

When a person's kidney function is about three percent (3%) of normal, the person is said to have end stage renal disease (ESRD). Continuous ambulatory peritoneal dialysis (CAPD) is a medical therapy used to remove the toxins that accumulate in the blood when the kidneys stop functioning. Peritoneal dialysis uses the person's peritoneal lining as a filter mechanism. The patient introduces dialysis solution into the peritoneal cavity through a surgically implanted catheter. To accomplish this form of dialysis, the patient leaves the solution in his or her peritoneal cavity for about 4 hours and then drains the solution out of the peritoneal cavity. During the time the dialysis solution is in the patient's peritoneum, the toxins in the patients blood streem diffuse through the peritoneal lining into the dialysis solution. When the solution is drained, the toxins are flushed from the peritoneum with the fluid. After draining the fluid, the patient repeats the procedure by again introducing fresh sterile solution into the peritoneal cavity to continuously remove toxins from the blood. The patient transfers the solution in and out of the peritoneal cavity 4 or more times per day. Currently, most patients transfer about 4 times per day.

There are several problems associated with using CAPD to treat ESRD. The main drawback is the increased risk of peritonitis. Peritonitis may be caused by infectious bacteria getting into the peritoneal cavity from the environment Other causes of peritonitis infection include organic matter entering the peritoneal cavity from the environment or non-dissolved solids entering the peritoneal cavity from the bags containing dialysis solution. According to United States Renal Data System (USRDS), there are 56% more deaths due to infection for patients using peritoneal dialysis therapy than for patients being treated using hemodialysis. According to the New England Journal of Medicine, peritonitis occurs once every 15 patient-months of dialysis. According to the USRDS some of the causes of peritonitis in CAPD patients are poor transfer technique, peritoneal access, less overall clearance of small uremic toxins, and possible deleterious effects of the dialysis fluid on the macrophage function.

A second problem associate with current CAPD procedures is the introduction of air into the peritoneal cavity. As the patient transfers fluid to and from the peritoneal cavity, air from the lines is flushed into the peritoneum. The air causes sharp pain in the shoulders and muscles of the patient until it is absorbed and removed. Depending upon the quantity of air, the pain can last from 20 minutes to several days. While air introduction is generally not life-threatening, it impacts significantly upon the quality of life of a dialysis patient.

Current technology relies upon the patient's technique to prevent introduction of bacteria, organic matter and air into the peritoneum; however, even with proper technique every transfer exposes the peritoneum to the surrounding environment. The more transfers that are performed, the greater the number of exposures. According to the USRDS and the New England Journal of Medicine, however, increasing the number of transfers and the volume of fluid moved through the peritoneum correspondingly increases the effectiveness of toxin clearance.

DISCLOSURE OF INVENTION

A novel filter of this invention uses an absolute membrane micro-filter to screen out all bacteria and virtually all the organic matter. Currently, commercially available 0.2 micron absolute membrane filters are considered to be satisfactory, but it is recognized that other sizes and types of filter media will also be operable for the practice of this invention. In practice, the filter may be attached to an implanted catheter for an interval encompassing several transfers, using aseptic technique. It is generally convenient and sufficient to change filters once per day. Once the filter has been put in place, the patient is free to transfer solution virtually anywhere and in any situation. The filter provides a barrier between the environment and the peritoneal cavity, as well as a barrier between the non-dissolved solids in the dialysis solutions and the patient's peritoneal cavity. It thereby addresses directly the causes of peritonitis. The effects of poor technique and the problems associated with peritoneal access are avoided to a great extent, because the patient need perform only one unprotected connection per several transfers (resulting in at least a 75% reduction in unprotected connections per day, assuming four transfers per day, using a single filter.) The filter may be sized to allow for five or more transfers per day to increase the toxin clearance. It maintains its protective properties throughout the day. It thus simply and efficiently eliminates the main problems associated with peritonitis.

The filter also eliminates the main cause of introduction of air into the peritoneal cavity. The first thing a patient does once the filter is attached is to drain the peritoneal cavity. The act of draining the peritoneal cavity primes the filter and effectively displaces any air in the filter between the patient and the filter membrane, including any air resident in the lines from the filter to the patient's peritoneal cavity. The filter is ideally structured so that it primes in any position or orientation. The priming is thus unaffected by technique, and is accomplished every time the peritoneal cavity is drained. The filter membrane provides a barrier against the passage of air from between the dialysis solution bag and the filter membrane into the patient. An air vent may be provided on the solution bag side of the filter to allow the air from the lines to escape as the fresh solution moves through the filter to the peritoneal cavity.

The present invention provides a medical filter constructed as a chamber, having an interior openly communicating with a patient connection structure adapted for connection to a dialysis solution flow fixture carried by a dialysis patient. The interior is also in open communication with a transport connection adapted for connection to external dialysis solution containment apparatus, generally a supply of fresh dialysis solution or a disposal container for spent dialysis solution. Support structure, mounted within the interior, is usually structured as a thin, perforated member, having a relatively very large support surface. Hydrophilic filter medium is mounted atop the support surface, and has a pore size capable of separating particulate materials, including bacteria, from fresh dialysis solution. First channel structure within the chamber defines a first flow path from the patient connection across the surface of the filter medium to the transport connection. Second channel structure within the chamber defines a second flow path from the transport connection through the filter medium and the perforated support structure to the patient connection. Flow control mechanism may also be mounted within the chamber and operable to direct fluid from the patient connection through the first flow channel and to direct fluid from the transport connection through the second flow channel.

A presently preferred embodiment of the invention comprises a container with an interior volume in open fluid communication with a patient connection element and a transport connection element. Filter support structure is mounted within the interior volume. This structure may include a plurality of filter elements arranged in approximately parallel stacked arrangement, whereby to define a plurality of approximately parallel flow paths straddling the filter elements. Each filter element includes first and second panel members, each having an exterior surface and an interior surface. Apertures extend between those exterior and interior surfaces. First and second edge members connect the panel members at the respective interior surfaces of the panel members, whereby to enclose an interior fluid flow zone within the filter element The edge members have exterior and interior surfaces and carry ports arranged to permit liquid to pass through the first edge member, through the flow zone between the opposed edge members and out the second edge member. Hydrophilic filter medium is mounted to the exterior surfaces of the first and second panel members to cover the perforations. Flow control structure within the interior volume is constructed and arranged to: (1) cause liquid introduced through the patient connection structure to flow through the first edge member, through the flow zone, out the second edge member, and then across the exterior surfaces of the panel members to the transport connection element; and (2) cause liquid introduced through the transport connection member to flow into the interior volume to surround the filter elements, through the filter medium into the interior zone and out the ports in the first edge member to the patient connection structure.

The chamber may have an interior defined by a bottom portion and a cover portion. Visualizing the bottom portion as a box, the filter support structure is mounted within the interior. The filter support structure may be visualized as being formed from spaced, perforated top and bottom panel members, joined by perforated edge members to define a space constituting an interior flow path (or zone) between the panel members. The first channel structure within the chamber may be considered to include first and second segments structured and arranged so that liquid from the patient connection is directed by the first segment, through the perforated edge members and across the interior flow path to the second segment. The second channel structure within the chamber is structured and arranged to direct liquid from the transport connection, around the exterior of the support structure, through the filter medium into the interior zone and through the perforated edge members to the patient connection. A flow control mechanism mounted within the chamber may be structured and arranged to permit liquid flow from the second segment to the interior, thereby providing for washing of all surfaces of the filter medium. The bottom portion may conveniently take the form of a substantially rectilinear box, and the filter support structure may be oriented to hold sheets of filter medium approximately parallel the direction of flow of liquid traveling from the patient connection towards the transport connection.

BRIEF DESCRIPTION OF DRAWINGS

In the drawings, which illustrate what is currently regarded as the best mode for carrying out the invention:

FIG. 1 is a diagrammatic representation of a first embodiment of the invention;

FIG. 2 is a diagrammatic representation of a second embodiment of the invention;

FIG. 3 is a pictorial view of a presently preferred embodiment of the invention;

FIG. 7 is a sectional view taken along the line 7—7 of FIG. 1, viewed in the direction of the arrows.

BEST MODES FOR CARRYING OUT THE INVENTION

Figure 4:
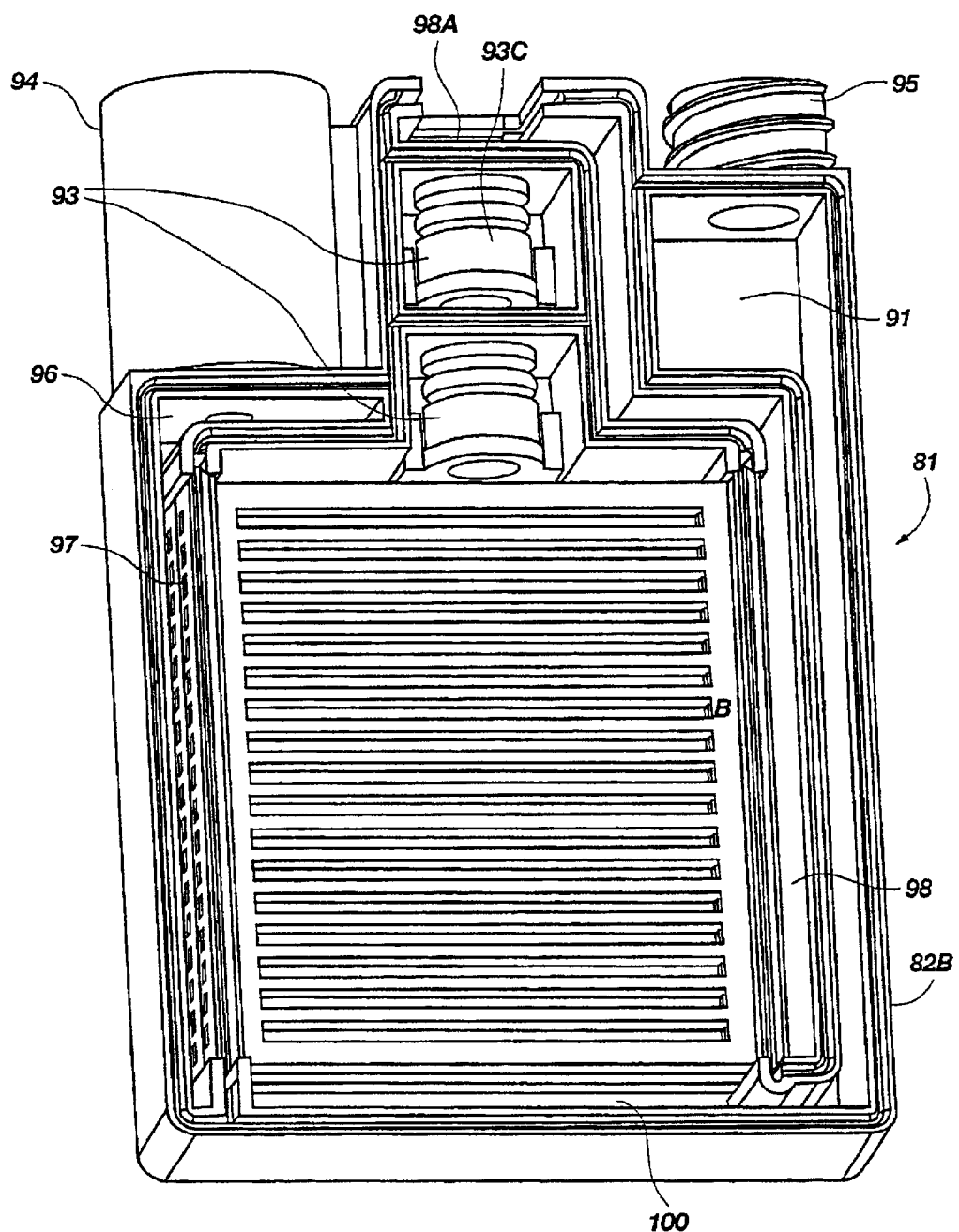
FIG. 4 is a view similar to FIG. 3, but with a cover portion removed to shown internal components.

FIG. 1 illustrates a filter, generally 11, of this invention, which includes a tube 13 that has multiple perforations 14 in a middle portion 15, being constructed of resilient material having physical properties selected to ensure that the tube 13 will retain its shape under a small stress and if deformed under a higher stress, will return to approximately its original shape once the stress has been removed. Filter material 17 is wrapped around the perforated tube 13 in a sealed relationship, such that all of the holes 14 in the perforated portion 15 are covered by a membrane of filter material 17. The filter material is hydrophilic, and allows the flow of liquid but constitutes a barrier against the flow of air. The holes 14 in the tube 13 are positioned within the region 15 between boundaries 19, 21 defined by circumferential sealed interfaces between the filter membrane 17 and the exterior surface of the tube 13. One end 23 of the perforated tube 13 is provided with a check valve 25 that allows flow only in a direction away from the patient's peritoneal cavity. The other end 27 of the perforated tube 13 is connected to an end cap 29. The end cap 29 has a connection 31 for attaching the filter 11 to the patient (not shown). The filter material, perforated tube, and check valve are encased in an outer cover 33 that may be either flexible or rigid. The outer cover 33 is provided with air vents 35 that permit the passage of air in either direction, but hydrophobic material 17 is positioned to cover the air vents so that neither bacteria nor other particulate materials are able to enter the filter 11. The hydrophobic material ideally comprises a 0.2 micron absolute filter material. The outer cover is provided with a fitting, such as an end cap 37, which includes a connection 39 structured appropriately for attaching the filter 11 to a pressure device (not shown), typically a pump conventional to CAPD procedures. The pressure device is preferably capable of adjusting the pressure in the filter 11 selectively to either above or below the pressure in the peritoneal cavity of the patient.

In a typical application, once the filter 11 is in place, with fixture 31 connected to tubing installed in the peritoneal cavity of a patient and connection 39 attached to a pump and waste container in conventional CAPD fashion, the peritoneal cavity is drained by operating the pump to reduce the pressure in the filter 11 to below the pressure in the peritoneal cavity. Fluid flows out of the peritoneum, through the perforated tube 13, through the check valve 25 and to a waste container (not shown), via connection 39. As fluid flows through the perforated tube 13, it sweeps air out of the perforated tube 13. The vacuum caused by the flowing fluid inherently pulls any air entrapped between the membrane 17 and the perforated tube 13 out past the check valve 25 and through the connection 39. This air removal will occur regardless of orientation of the filter 11. Virtually no fluid from the perforated tube will flow across the membrane and into the outer cavity 41 of the filter 11 due to the vacuum pressure created by the pump. The flow will be substantially out connection 39 (to the pump) and then (from the pump) to suitable waste container (typically a conventional drain bag- the pressure from the pump to the drain bag is inherently positive). When the vacuum is removed, air will not flow back into the perforated tube 13 due to the check valve 25. The filter material is permeable to water and not air, so air can not flow through the filter material, through the perforations in the tube and into the perforated tube 13.

The usual second step of the CAPD procedure is to fill the peritoneal cavity with fresh fluid. A fresh fluid supply is thus attached to connection 39, ideally through through a pump, and the pressure of the fresh fluid supply is increased to higher than the pressure in the peritoneal cavity. The increased pressure causes the fluid to flow into the filter 11, through connection 39 and through check valve 43 toward the peritoneal cavity. As the fresh fluid flows into the filter 11, flow directly into the perforated tube 13 is blocked by the check valve 25. The fluid is diverted to flow around the filter material 17 and is forced through the filter material 17 (removing any bacteria and non-dissolved solids) and into the perforated tube 13 through the perforations 14. The liquid flows out of the perforated tube 13 and into the patient's peritoneum, via fixture 31. Any air entering the filter with the fluid is also diverted to the chamber surrounding the filter material. This air escapes via the air vents 35 in the outer cover 33.

The arrangement illustrated by FIG. 2 is generally similar to that described in connection with FIG. 1. The illustrated filter, generally 49, is configured somewhat differently than the filter 11 (FIG. 1), but its operation is similar. As illustrated, an end cap fitting 51 connects to tubing surgically installed to communicate with a patient's peritoneal cavity. A "Tee" fitting 53 is connected through appropriate tubing to a pump. The peritoneal cavity is drained by operating the pump to reduce the pressure in the filter 49 to below the pressure in the peritoneal cavity. Fluid flows out of the peritoneum, through the perforated tube 55, through a first check valve 57 and through the Tee fitting 53. Air is inherently swept from the filter 49 by the vacuum caused by the flowing fluid. Virtually no fluid from the perforated tube 55 flows across the filter medium 59 into the chamber 61 of the filter 49. When the vacuum is removed, air will not flow back into the perforated tube 55 due to the check valve 57.

The peritoneal cavity is supplied with fresh fluid introduced to the Tee connection 53. Fluid flow is through the connection 53, the check valve 63, the chamber 61, through the filter medium 59, the perforations 65 in the tube 55 and to the peritoneal cavity via fixture 51. The end caps 67, 69, the outer cover 71 and the air vent 73 all function as described in connection with FIG. 1, although their respective configurations are harmonized with the overall structure of the filter 49.

The filter, generally 81 illustrated by FIGS. 3 through 7 is presently preferred because of its compact, convenient size and shape. Moreover, the fluid flow paths with respect to the surface of the filter medium offer some additional therapeutical advantages to the dialysis patient. Practical filters of this design may be contained within a housing measuring approximately one half by two by three inches; a specific example measuring about 0.6 inches high by 2.893 inches long by 1.943 inches wide.

Figure 5:
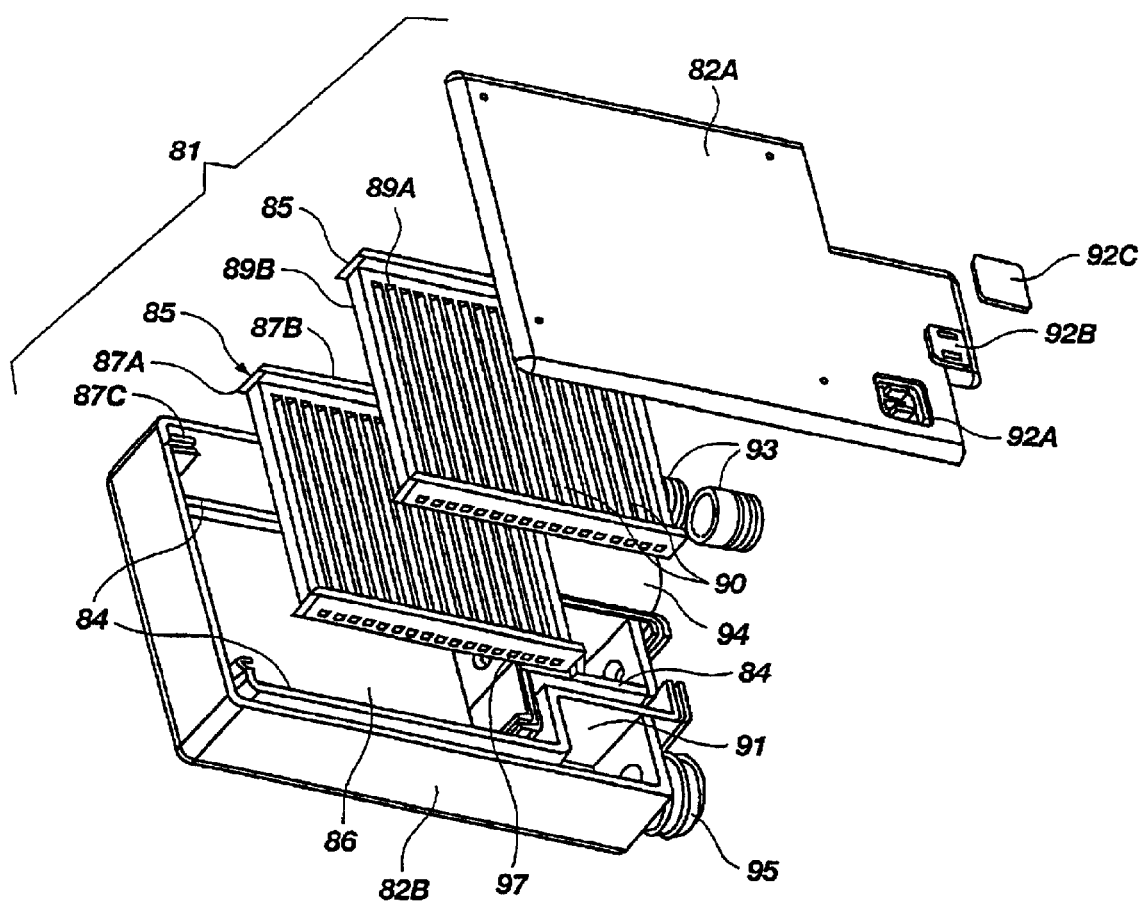
FIG. 5 is an exploded view of the filter of FIGS. 3 and 4.
Figure 6:
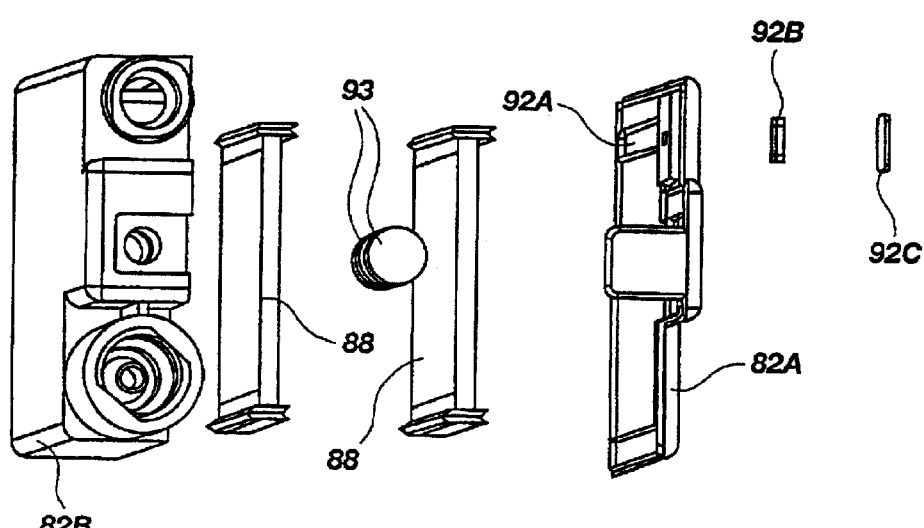
FIG. 6 is an exploded perspective view rotated to illustrate certain of the components shown by FIG. 5 from a different angle and to illustrate additional components of the filter of FIGS. 3 and 4.

As best shown by FIG. 5, a housing, 82, comprises a cover portion 82A and a box portion 82B. The interior of the box 82B is divided by interior walls 84 to provide flow channels. Filter support structures, generally 85, are positioned in stacked arrangement within a relatively large chamber 86. As illustrated, a pair of filter supports 85 are held by means of end extensions 87A of side rails 87B registered within support channels 88. It is within contemplation that a single filter support or a greater plurality of filter supports be incorporated in other specific embodiments of the invention. In any case, appropriate filter medium 88 (FIG. 6) may be positioned upon either or both the upper and lower surfaces 89A, 89B of the supports 85. This medium may conveniently take the form of flat sheets of medical filtration membrane material capable of removing fine particles, bacteria, virus and fungi from aqueous solutions. One suitable such material is the hydrophilic polyethersulfone membrane material sold under the trademark "Supor"® by Pall Corporation, 2200 Northern Boulevard, East Hills, N.Y. 11548. While this material is available with either smaller or larger pore sizes, a pore size of 0.2 µm is currently preferred. In the illustrated instance, a single thickness of the filter membrane (not shown) is positioned against each surface 89A and 89B of both supports 85 to cover the apertures 90.

The box portion 82B includes a smaller chamber 91, which registers with an air vent 92A in the cover 82A. A resilient check valve, such as the silicone panel 92B illustrated, is positioned within the vent 92A beneath a dust cover 92C. This assembly permits air to escape from the chamber 91. An appropriate mechanism, such as a hydrophobic membrane (not visible) is positioned across the vent 92 A to block liquid flow. One suitable mechanism for this purpose is a single thickness of the PTFE membrane sold by Pall Corporation, 2200 Northern Boulevard, East Hills, N.Y. 11548 attached to the inner surface of the cover 82A to cover the vent 92A.

Flow control mechanism, such as the redundant check valves 93 illustrated, direct dialysis solution entering from the sterile (patient) side connection 94 across the surfaces of the filter sheets 88 towards the non-sterile (pump) side connection 95. In operation, spent dialysis solution drains from the patient through connection 94 into flow channel 96 from which it is displaced through apertures 97 and across the inner surfaces of filter medium 88 (FIG. 6), carried by the supports 85 into flow channel 98. At the end 98A of the flow channel 98, solution advances against the closed end 93A of the first valve 93, thereby opening the port 99. Solution then flows into the valve chamber 93B, causing the soft, resilient portion 93C (FIG. 4) to compress, thereby opening the flow path 93D. The second check valve 93 is optional, but if present, operates in exactly the same fashion. The check valves 93 thus function to direct the solution to flow channels 100A, 100B, 100C across the outer surfaces of the filter medium 88.

As a consequence of this flow path, the surfaces of the filter medium 88 are washed by flowing spent dialysis solution prior to the introduction of fresh dialysis solution, thereby diluting and removing pyrogens and endotoxins, as well as air. Solution eventually flows into the flow channel 101, from which it eventually flows through the chamber 91 and out through the connection 95 to a suitable disposal site (usually a bag.)

Fresh dialysis solution is introduced through the connection 95, from which it flows into the flow channel 101, and then fills the compartment 86 (FIG. 5). The check valves 93 prevent flow out of the compartment 86, except through the perforations 97. This travel path inevitably force all of the fresh solution to pass through filter medium to the interior of the supports 85. Except for a small volume of solution which remains trapped in the channel 98, the fresh solution flows to the channel 96 and then to the patient through the connection 94.

The chamber 91 may include structure (not shown) constructed and arranged to function as a pressure regulator for both stages of a dialysis solution transfer. It is contemplated that a filter embodied as shown by FIGS. 3 through 7 will be used for a 24 hour period and then replaced with a similar filter. The illustrated embodiment has a capacity reasonably adequate for up to six typical cycles, although its effective useful life may be longer under emergency circumstances.

Reference in this disclosure to features of the illustrated embodiments is not intended to limit the scope of the appended claims, which themselves define the invention claimed. The invention may be embodied in various configurations, and each of its constituent parts may be replaced with other structures having equivalent characteristics or functions.

INDUSTRIAL APPLICABILITY

The filter of this invention is primarily useful for medical applications, and particularly in connection with CAPD procedures.

What is claimed is:

1. A medical filter, comprising
   a chamber, having
      an interior,
      a patient connection, in open fluid communication with said interior and adapted for connection to a dialysis solution flow fixture carried by a dialysis patient,
      a transport connection, in open fluid communication with said interior and adapted for connection to external dialysis solution containment apparatus;
   support structure, mounted within said interior, structured as a thin, perforated member, having a support surface;
   hydrophilic filter medium mounted atop said support surface, having a pore size capable of separating particulate materials from fresh dialysis solution;
   first channel structure within said chamber defining a first flow path from said patient connection across the surface of said filter medium to said transport connection;
   second channel structure within said chamber defining a second flow path from said transport connection through said filter medium and said support structure to said patient connection; and
   flow control mechanism mounted within said chamber and operable to direct fluid from said patient connection through said first channel structure and to direct fluid from said transport connection through said second channel structure;
   wherein said second channel structure includes a portion in communication with an air vent structure constructed and arranged to release air from solution flowing through said interior while retaining said solution within said interior.

2. A medical filter according to claim 1, wherein said air vent structure includes a hydrophobic membrane positioned in the travel path of air through said vent structure.

3. A medical filter according to claim 1 comprising
   a chamber, having
      an interior,
      a patient connection, in open fluid communication with said interior and adapted for connection to a dialysis solution flow fixture carried by a dialysis patient, and
      a transport connection, in open fluid communication with said interior and adapted for connection to external dialysis solution containment apparatus;
   support structure, mounted within said interior, structured as a thin, perforated member, having a support surface;
   hydrophilic filter medium mounted atop said support surface, having a pore size capable of separating particulate materials from fresh dialysis solution;
   first channel structure within said chamber defining a first flow path from said patient connection across the surface of said filter medium to said transport connection;
   second channel structure within said chamber defining a second flow path from said transport connection through said filter medium and said support structure to said patient connection; and
   flow control mechanism mounted within said chamber and operable to direct fluid from said patient connection through said first channel structure and to direct fluid from said transport connection through said second channel structure;
   wherein said support structure comprises an inner conduit, with an open interior defined by a first wall, having a first end, a second end and a perforated section between said first and second ends;
   said first channel structure is structured to accommodate flow through said inner conduit;
   said flow control mechanism comprises a check valve positioned at said second end, structured and arranged to permit flow from said inner conduit through said transport connection;
   said inner conduit is positioned with an outer housing structured and arranged to define said second channel structure exterior of said perforated section;
   said filter medium is positioned adjacent said perforated section such that fluid flow from said fluid passageway to said open interior must pass through said medium; and
   said flow control mechanism further comprises valve means at said first end, structured and arranged to permit fluid flow from said second channel structure, through said perforated section, through said open interior and out said patient connection.

4. A medical filter according to claim 3, wherein said second channel structure includes a portion in communication with an air vent structure constructed and arranged to release air from solution flowing through said interior while retaining said solution within said interior.

5. A medical filter according to claim 4, wherein said air vent structure includes a hydrophobic membrane positioned in the travel path of air through said vent structure.

6. A medical filter comprising
   a chamber, having
      an interior,
      a patient connection, in open fluid communication with said interior and adapted for connection to a dialysis solution flow fixture carried by a dialysis patient,
      a transport connection, in open fluid communication with said interior and adapted for connection to external dialysis solution containment apparatus;

support structure, mounted within said interior, structured as a thin, perforated member, having a support surface;

hydrophilic filter medium mounted atop said support surface, having a pore size capable of separating particulate materials from fresh dialysis solution;

first channel structure within said chamber defining a first flow path from said patient connection across the surface of said filter medium to said transport connection;

second channel structure within said chamber defining a second flow path from said transport connection through said filter medium and said support structure to said patient connection; and flow control mechanism mounted within said chamber and operable to direct fluid from said patient connection through said first channel structure and to direct fluid from said transport connection through said second channel structure;

wherein said filter medium comprises thin sheet material configured to cover the perforations of said support structure.

7. A medical filter according to claim 6, wherein said filter medium comprises a micro porous membrane.

8. A medical filter according to claim 7, wherein said membrane has a pore size of approximately 0.2 μm.

9. A medical filter according to claim 7, wherein said membrane is constructed of polyethersulfone.

10. A medical filter according to claim 9, wherein said membrane has a pore size of approximately 0.2 μm.

11. A medical filter comprising
  a chamber, having
    an interior,
    a patient connection, in open fluid communication with said interior and adapted for connection to a dialysis solution flow fixture carried by a dialysis patient,
    a transport connection, in open fluid communication with said interior and adapted for connection to external dialysis solution containment apparatus;
  support structure, mounted within said interior, structured as a thin, perforated member, having a support surface;
  hydrophilic filter medium mounted atop said support surface, having a pore size capable of separating particulate materials from fresh dialysis solution;
  first channel structure within said chamber defining a first flow path from said patient connection across the surface of said filter medium to said transport connection;
  second channel structure within said chamber defining a second flow path from said transport connection through said filter medium and said support structure to said patient connection; and
  flow control mechanism mounted within said chamber and operable to direct fluid from said patient connection through said first channel structure and to direct fluid from said transport connection through said second channel structure;
  wherein said chamber has an interior defined by a bottom portion and a cover portion,
  said support structure mounted within said interior is formed from spaced, perforated top and bottom panel members, joined by perforated edge members to define a space constituting an interior flow path between said panel members;
  said first channel structure within said chamber includes first and second segments structured and arranged so that liquid from said patient connection is directed by said first segment, through said perforated edge members and across said interior flow path to said second segment; and
  said second channel structure within said chamber is structured and arranged to direct liquid from said transport connection, around the exterior of said support structure, through said filter medium into said space and through said perforated edge members to said patient connection; and
  said flow control mechanism mounted within said chamber is structured and arranged to permit liquid flow from said second segment to said interior.

12. A medical filter according to claim 11, wherein said bottom portion is a substantially rectilinear box and said support structure is oriented to hold sheets of filter medium approximately parallel the direction of flow of liquid traveling from said patient connection towards said transport connection.

13. A medical filter according to claim 11, wherein said flow control mechanism is positioned in fluid flow communication with said second segment of said first channel structure, and is arranged to direct liquid from said second segment to the exterior of said support structure.

14. A medical filter according to claim 11, including a plurality of said support structures mounted in spaced parallel relationship within said chamber.

15. A medical filter according to claim 14, wherein said bottom portion is a substantially rectilinear box and said support structures are each oriented to hold sheets of filter medium approximately parallel the direction of flow of liquid traveling from said patient connection towards said transport connection.

16. A medical filter according to claim 14, wherein said flow control mechanism is positioned in fluid flow communication with said second segment of said first channel structure, and is arranged to direct liquid from said second segment to flow parallel, between and across the exteriors of said support structures.

17. A medical filter according to claim 16, wherein said second channel structure includes a portion in communication with an air vent structure constructed and arranged to release air from solution flowing through said interior while retaining said solution within said interior.

18. A medical filter according to claim 17, wherein said air vent structure includes a hydrophobic membrane positioned in the travel path of air through said vent structure.

19. A medical filter, comprising
  an inner conduit, with an open interior defined by a first wall, having a first end, a second end and a perforated section between said first and second ends;
  a flow channel at said first end, structured to accommodate flow into or out of said inner conduit;
  a check valve at said second end, structured and arranged to permit flow from said inner conduit;
  an enclosure for said inner conduit, structured and arranged to define a fluid passageway exterior said perforated section;
  a filter medium positioned adjacent said perforated section such that fluid flow from said fluid passageway to said open interior must pass through said medium, said medium being hydrophilic and capable of blocking bacterial-sized particles; and
  valve means at said first end, structured and arranged to permit fluid flow from said open interior but to direct fluid flowing in the opposite direction into said fluid passageway.

20. A medical filter, comprising a container with an interior volume in open fluid communication with a patient connection element and a transport connection element;

filter support structure mounted within said interior volume and including a plurality of filter elements arranged in approximately parallel stacked arrangement, whereby to define a plurality of approximately parallel flow paths straddling said filter elements, each said filter element including first and second panel members, each having an exterior surface and an interior surface with apertures extending between said exterior and interior surfaces, first and second edge members connecting said panel members at the respective interior surfaces of said panel members, whereby to enclose an interior fluid flow zone within said filter element, said edge members having exterior and interior surfaces and carrying ports arranged to permit liquid to pass through said first edge member, through said flow zone between opposed said edge members and out said second edge member, hydrophilic filter medium mounted to the exterior surfaces of said first and second panel members to cover said apertures; and flow control structure within said interior volume constructed and arranged to:

cause liquid introduced through said patient connection element to flow through said first edge member, through said zone, out said second edge member, and then across said exterior surfaces of said panel members to said transport connection element; and cause liquid introduced through said transport connection element to flow into said interior volume to surround said filter elements, through said filter medium into said interior zone and out said ports in said first edge member to said patient connection element.

21. A medical filter according to claim 20, further including a channel structure having a portion in communication with an air vent structure constructed and arranged to release air from a solution flowing through said interior volume while retaining said solution within said interior volume.

22. A medical filter according to claim 21, wherein said air vent structure includes a hydrophobic membrane positioned in the travel path of air through said vent structure.

23. A medical filter according to claim 20, wherein said filter medium comprises thin sheet material configured to cover the perforations of said support structure.

24. A medical filter according to claim 23, wherein said filter medium comprises a micro porous membrane.

25. A medical filter according to claim 24, wherein said membrane has a pore size of approximately 0.2 $\mu$m.

26. A medical filter according to claim 24, wherein said membrane is constructed of polyethersulfone.

27. A medical filter according to claim 26, wherein said membrane has a pore size of approximately 0.2 $\mu$m.

* * * * *